US010390776B2

(12) United States Patent
Fuh et al.

(10) Patent No.: US 10,390,776 B2
(45) Date of Patent: Aug. 27, 2019

(54) THREE-DIMENTIONAL SERIAL FOCUSED INTRAORAL DIGITAL TOMOSYNTHESIS SCANNER AND CONTROLLING METHOD THEREOF

(71) Applicant: China Medical University, Taichung (TW)

(72) Inventors: Lih-Jyh Fuh, Taichung (TW);
Yen-Wen Shen, Taichung (TW);
Heng-Li Huang, Taichung (TW);
Jui-Ting Hsu, Taichung (TW);
Che-Wei Liao, Taichung (TW)

(73) Assignee: China Medical University, Taichung (TW)

( * ) Notice: Subject to any disclaimer, the term of this patent is extended or adjusted under 35 U.S.C. 154(b) by 238 days.

(21) Appl. No.: 15/684,957

(22) Filed: Aug. 24, 2017

(65) Prior Publication Data

US 2018/0055463 A1 Mar. 1, 2018

(30) Foreign Application Priority Data

Aug. 26, 2016 (TW) .............................. 105127534 A
May 19, 2017 (TW) .............................. 106116748 A

(51) Int. Cl.
*A61B 6/14* (2006.01)
*A61B 6/02* (2006.01)
*A61B 6/00* (2006.01)

(52) U.S. Cl.
CPC .............. *A61B 6/145* (2013.01); *A61B 6/025* (2013.01); *A61B 6/027* (2013.01); *A61B 6/40* (2013.01); *A61B 6/42* (2013.01); *A61B 6/4435* (2013.01); *A61B 6/4452* (2013.01); *A61B 6/5235* (2013.01)

(58) Field of Classification Search
CPC ......... A61B 6/025; A61B 6/027; A61B 6/145; A61B 6/40; A61B 6/42; A61B 6/4435; A61B 6/4452; A61B 6/5235
See application file for complete search history.

(56) References Cited

U.S. PATENT DOCUMENTS

| 4,365,340 A | 12/1982 | Nishikawa et al. |
| 5,090,047 A | 2/1992 | Angotti et al. |
| 5,511,106 A | 4/1996 | Doebert et al. |

(Continued)

FOREIGN PATENT DOCUMENTS

WO 02086619 A1 10/2002

*Primary Examiner* — Marcus H Taningco

(57) ABSTRACT

A three-dimensional serial focused intraoral digital tomosynthesis scanner includes a frame body, an image capturing module, a photosensitive member and an image processing module. The frame body includes a central axis and a light source seat which is moved along a scanning path and rotated around the central axis. The image capturing module is disposed on the light source seat and reciprocated along the scanning path. The image capturing module is configured to generate a light beam emitted from an outside to the patient's mouth. The photosensitive member is positioned in the patient's mouth. The light beam is emitted to the photosensitive member and moved along the scanning path corresponding to the photosensitive member so as to generate a plurality of two-dimensional optical images by the image capturing module. The image processing module calculates the two-dimensional optical images to generate a three-dimensional image.

20 Claims, 15 Drawing Sheets

(56) References Cited

U.S. PATENT DOCUMENTS

| | | | | |
|---|---|---|---|---|
| 5,995,583 | A * | 11/1999 | Schick | A61C 9/0073 378/191 |
| 6,118,842 | A * | 9/2000 | Arai | A61B 6/032 378/38 |
| 2006/0067483 | A1 | 3/2006 | Hack et al. | |
| 2007/0058786 | A1* | 3/2007 | Michael | A61B 6/14 378/207 |
| 2009/0245461 | A1 | 10/2009 | Lee | |
| 2015/0036797 | A1* | 2/2015 | Nachaliel | A61B 6/4057 378/38 |
| 2016/0287198 | A1* | 10/2016 | Abramovich | A61B 6/105 |
| 2016/0338657 | A1* | 11/2016 | Kim | A61B 6/4429 |
| 2017/0105686 | A1* | 4/2017 | Alric | A61B 6/032 |
| 2018/0206802 | A1* | 7/2018 | Heo | G03B 42/00 |
| 2018/0303442 | A1* | 10/2018 | Olsen | A61B 6/145 |

* cited by examiner

THREE-DIMENTIONAL SERIAL FOCUSED INTRAORAL DIGITAL TOMOSYNTHESIS SCANNER AND CONTROLLING METHOD THEREOF

RELATED APPLICATIONS

This application claims priority to Taiwan Application Serial Number 105127534, filed Aug. 26, 2016, and Taiwan Application Serial Number 106116748, filed May 19, 2017, which are herein incorporated by reference.

BACKGROUND

Technical Field

The present disclosure relates to a three-dimensional serial focused intraoral digital tomosynthesis scanner. More particularly, the present disclosure relates to a three-dimensional serial focused intraoral digital tomosynthesis scanner for capturing plural two-dimensional images to generate a three-dimensional image.

Description of Related Art

X-rays are used in a variety of industrial, scientific and medical fields to produce radiographic images. A radiographic image may be useful to display areas of different density and composition. X-rays are used, for example, in medical applications to distinguish bone from tissue. As x-rays are passed through an object and captured by a specific film or a digital sensor, a two-dimensional representation of all the intervening objects between the x-ray source and the sensor are provided.

In general, in the field of dentistry, there are various conventional imaging methods which have been proposed to use a dental X-ray imaging system for dental treatment or orthodontics, such as panoramic x-ray, periapical film, cephalometric film, computed tomography (CT) and cone-beam computed tomography (CBCT). In the case of periapical film, it has the advantage that the size of the device is small without requiring huge and complicated spaces, and its device has the features of low cost and lower radiation dose. However, the conventional periapical film can only output two-dimensional images. On the other hand, in the case of CT or CBCT technique, it has the advantage that the device can output three-dimensional images, and its device has the features of lower radiation dose, shorter acquisition time, higher resolution and more affordable cost.

Various existing systems and techniques construct three-dimensional representations of 2-D radiographic images. For example, in the dental setting, current 3-D radiography systems are provided using CT and CBCT techniques. With both techniques, an x-ray imaging system revolves around an axis relative to an area of interest, such as by rotating 360 degrees (or more) around the patient and taking 180 to 360 separate x-ray exposures per revolution. These types of systems use excessive amounts of radiation to capture a large area of interest (e.g., a patient's entire mouth), and are generally not designed to be focused on a particular area of interest. However, all medical devices should be configured to comply with the ALARA principle (As Low As Reasonably Achievable), and there is still considerable room for improvement in CT and CBCT techniques. Moreover, in the case of conventional CBCT technique, the typical resolution mostly used is between 70 um to 400 um, and it is still not enough to meet clinical requirements. Additionally, such 3-D radiography systems are generally very expensive, and not suited for the most common procedures that occur in general dentistry practice settings. Thus, there are general needs to produce high quality three-dimensional reconstructions of radiographic images with reduced radiation exposure, and at a reduced cost and complexity.

SUMMARY

According to one aspect of the present disclosure, a three-dimensional serial focused intraoral digital tomosynthesis scanner for scanning a patient's mouth includes a frame body, an image capturing module, a photosensitive member and an image processing module. The frame body includes a central axis and a light source seat. The light source seat is moved along a scanning path and rotated around the central axis. The image capturing module is disposed on the light source seat and reciprocated along the scanning path. The image capturing module is configured to generate a light beam emitted from an outside to the patient's mouth. The photosensitive member is connected to the frame body and positioned in the patient's mouth. The light beam is emitted to the photosensitive member. The light beam is moved along the scanning path corresponding to the photosensitive member so as to generate a plurality of two-dimensional optical images by the image capturing module, and the photosensitive member has a flaky shape. The image processing module is electrically connected to the image capturing module. The image processing module receives the two-dimensional optical images and calculates the two-dimensional optical images to generate a three-dimensional image.

According to another aspect of the present disclosure, a controlling method of the three-dimensional serial focused intraoral digital tomosynthesis scanner provides a position adjusting step, an image capturing step and an image processing step. The position adjusting step is for moving the image capturing module to a scanning position by the frame body so as to allow the image capturing module to correspond to the photosensitive member. The image capturing step is for generating the light beam emitted from the outside to the patient's mouth and moving the light beam along the scanning path corresponding to the photosensitive member so as to generate the two-dimensional optical images by the image capturing module. The image processing step is for calculating the two-dimensional optical images to generate the three-dimensional image by the image processing module.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
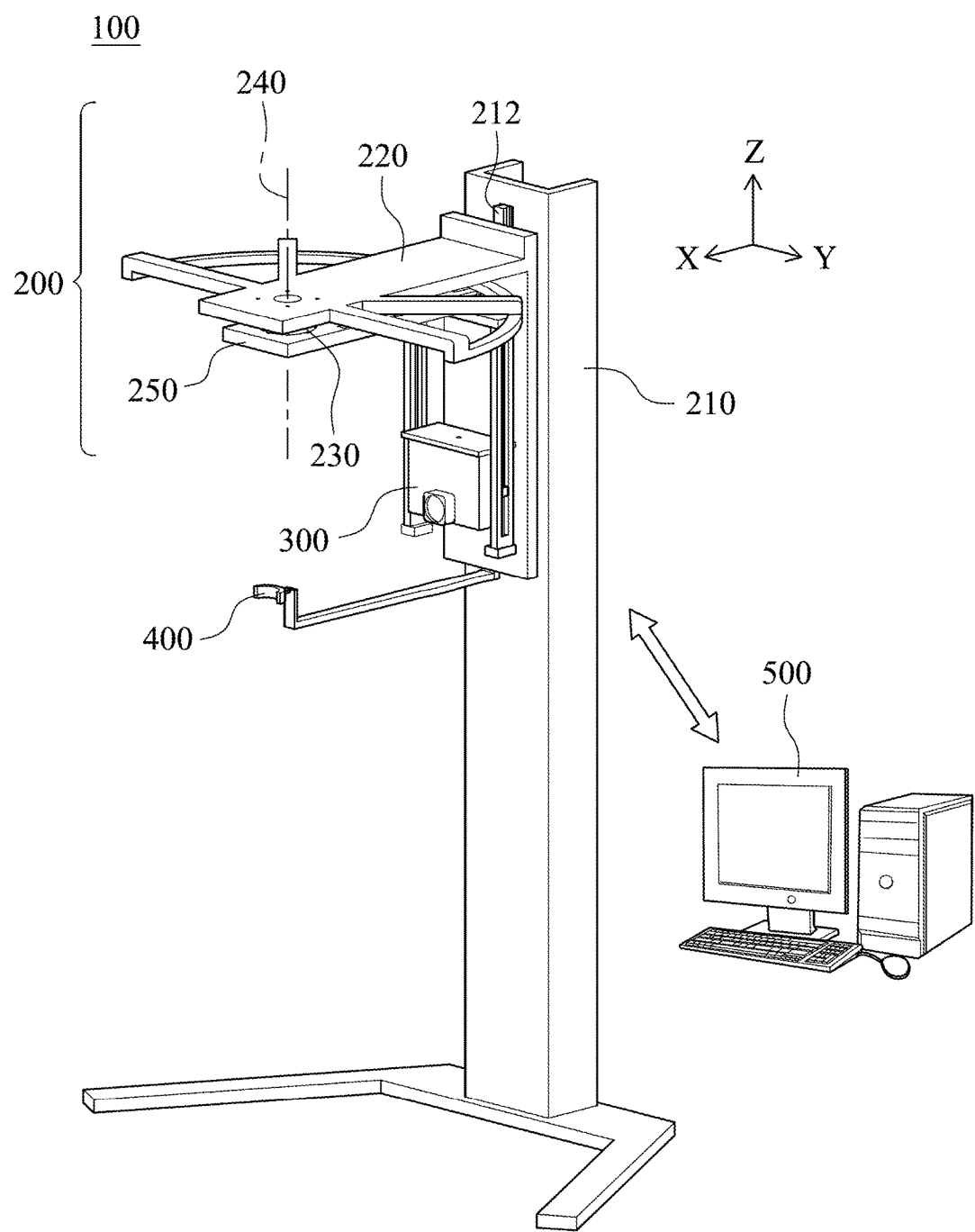
FIG. 1 shows a schematic view of a three-dimensional serial focused intraoral digital tomosynthesis scanner according to one embodiment of the present disclosure.
Figure 2:
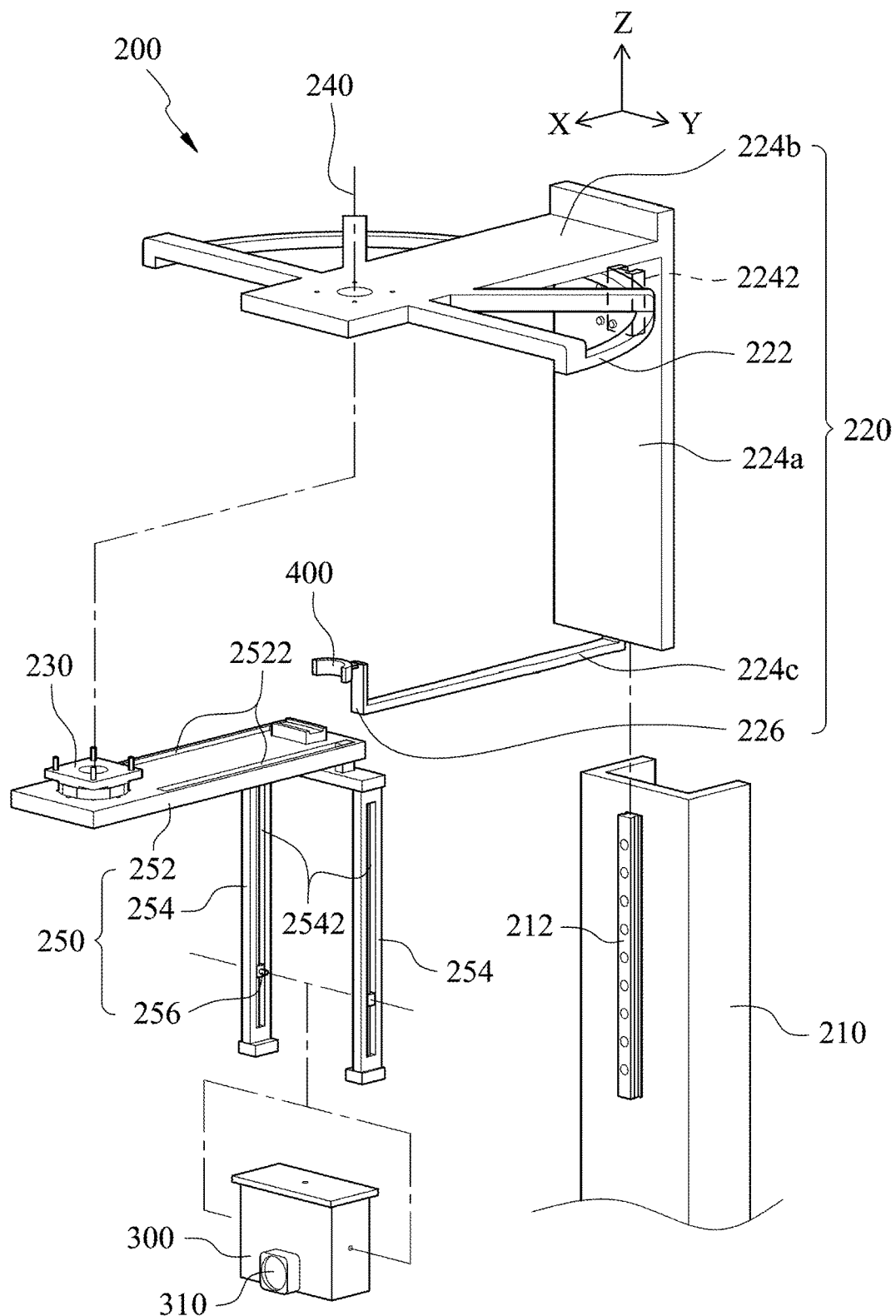
FIG. 2 shows an exploded view of the three-dimensional serial focused intraoral digital tomosynthesis scanner of FIG. 1.
Figure 3:
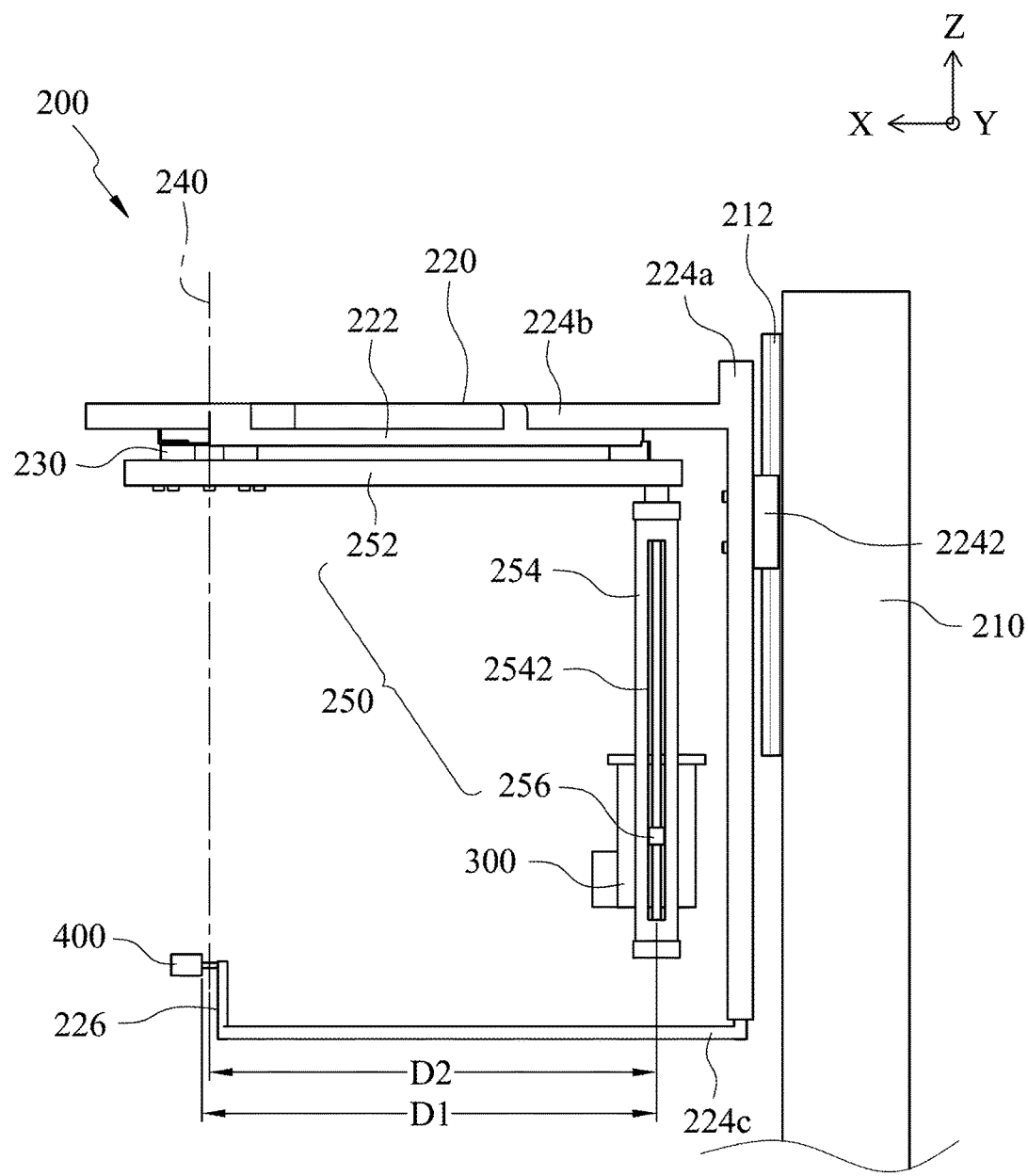
FIG. 3 shows a schematic side view of the three-dimensional serial focused intraoral digital tomosynthesis scanner of FIG. 1.
Figure 4:
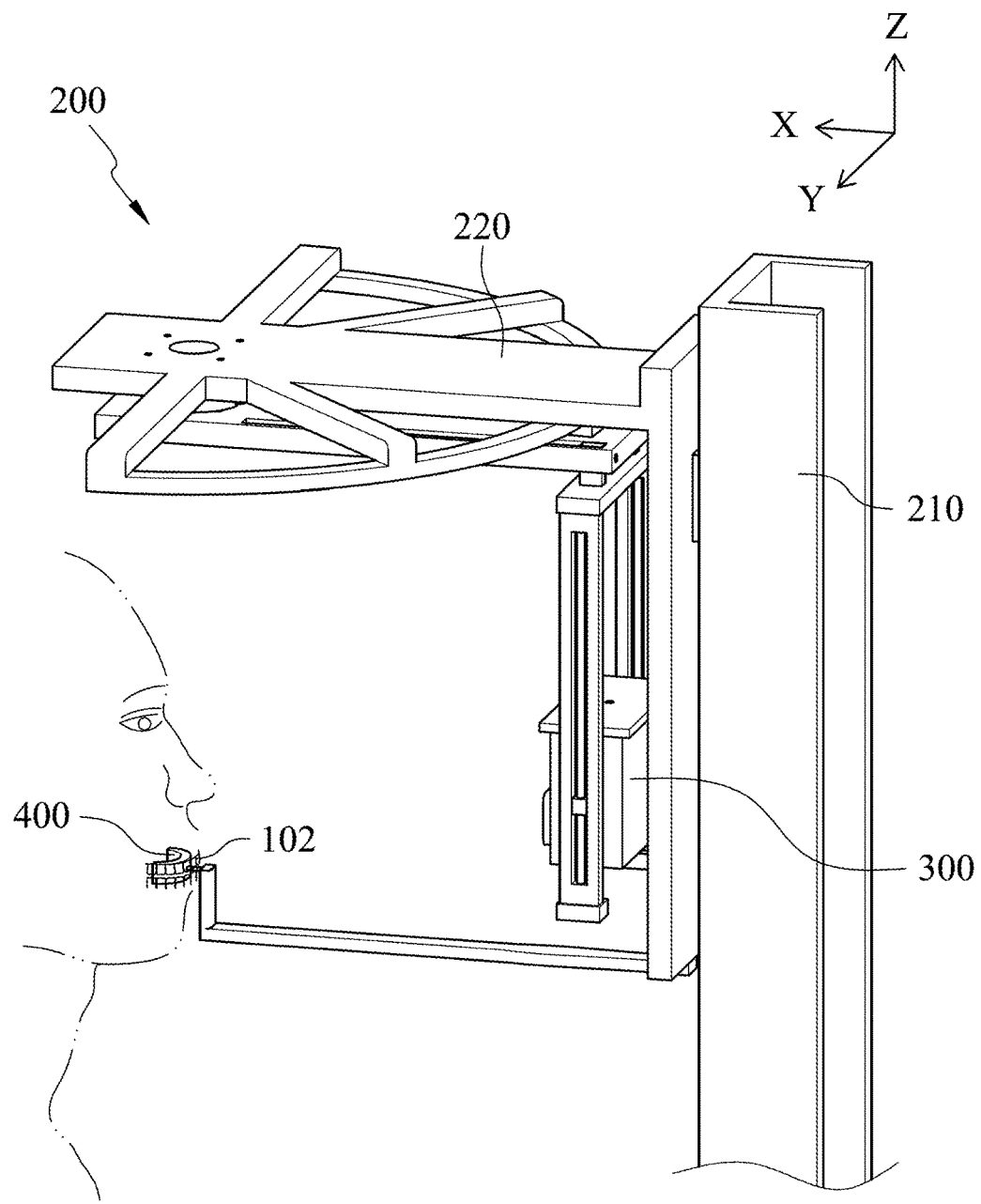
FIG. 4 shows a schematic view of an operation of the three-dimensional serial focused intraoral digital tomosynthesis scanner of FIG. 1.

FIG. 1 shows a schematic view of a three-dimensional serial focused intraoral digital tomosynthesis scanner 100 according to one embodiment of the present disclosure; FIG. 2 shows an exploded view of the three-dimensional serial focused intraoral digital tomosynthesis scanner 100 of FIG. 1; FIG. 3 shows a schematic side view of the three-dimensional serial focused intraoral digital tomosynthesis scanner 100 of FIG. 1; and FIG. 4 shows a schematic view of an operation of the three-dimensional serial focused intraoral digital tomosynthesis scanner 100 of FIG. 1. The three-dimensional serial focused intraoral digital tomosynthesis scanner 100 includes a frame body 200, an image capturing module 300, a photosensitive member 400 and an image processing module 500. The three-dimensional serial focused intraoral digital tomosynthesis scanner 100 is used to scan a patient's mouth to obtain plural two-dimensional images of a tooth 102. The two-dimensional images can be captured by moving the image capturing module 300 to different positions relative to the photosensitive member 400 and the tooth 102 of the patient's mouth. Then, the two-dimensional images are calculated to generate a three-dimensional image by the image processing module 500, thereby not only achieving a dental diagnosis with high resolution and lower radiation dose, but also having a simple structure, low cost and easy operation.

The frame body 200 includes a frame seat 210, a displacement member 220, a rotating electrical device 230, a central axis 240 and a light source seat 250. The frame seat 210 includes a track 212 extending in a Z-axis direction. The displacement member 220 is movably connected to the frame seat 210 and positioned on the track 212 by a positioning member 2242. In other words, the positioning member 2242 is movably connected between the track 212 and the displacement member 220. The photosensitive member 400 is disposed on the displacement member 220. In FIG. 2, the track 212 is a linear slide assembly to be capable of controlling movement and positions of the displacement member 220, the rotating electrical device 230 and the light source seat 250. The displacement member 220 includes a swinging track 222 having a semicircular shape and connected to the light source seat 250. The light source seat 250 is rotated around the central axis 240 at a rotating angle and configured to swing along the swinging track 222. The rotating angle is smaller than or equal to 180 degrees. Moreover, the displacement member 220 includes a first interlocking portion 224a, a second interlocking portion 224b, a third interlocking portion 224c and a fixing seat 226. The first interlocking portion 224a is connected to the track 212. The extending direction of the first interlocking portion 224a is parallel to the Z-axis direction. The second interlocking portion 224b is connected to one end of the first interlocking portion 224a. An extending direction of the second interlocking portion 224b is perpendicular to the Z-axis direction, and the rotating electrical device 230 is disposed on the second interlocking portion 224b. The third interlocking portion 224c is connected to the other end of the first interlocking portion 224a. An extending direction of the third interlocking portion 224c is parallel to the extending direction of the second interlocking portion 224b. The fixing seat 226 is connected between the third interlocking portion 224c and the photosensitive member 400. The fixing seat 226 is connected to a central portion of the photosensitive member 400. In addition, the light source seat 250 is moved along a scanning path and includes a pivotable swinging arm 252, a supporting frame 254 and a rotating shaft 256. The pivotable swinging arm 252 is connected to the rotating electrical device 230. The supporting frame 254 is connected to the pivotable swinging arm 252. The image capturing module 300 is movably disposed on the supporting frame 254. The pivotable swinging arm 252 is rotated by the rotating electrical device 230 to allow the image capturing module 300 to reciprocate along the scanning path so as to move a light beam generated by the image capturing module 300 along the scanning path. Furthermore, the swinging track 222 of the displacement member 220 is connected to the pivotable swinging arm 252 of the light source seat 250. The pivotable swinging arm 252 is rotated around the central axis 240 at the rotating angle and configured to swing along the swinging track 222. The central axis 240 is a virtual axis line parallel to the Z-axis direction. The pivotable swinging arm 252, the supporting frame 254 and the image capturing module 300 are synchronously rotated between the second interlocking portion 224b and the third interlocking portion 224c by the rotating electrical device 230.

Moreover, the pivotable swinging arm 252 includes two frame moving tracks 2522 parallel to each other, and the supporting frame 254 is restrictedly moved along the two frame moving tracks 2522. The supporting frame 254 includes two module moving tracks 2542. The image capturing module 300 is restrictedly moved along the two module moving tracks 2542. An extending direction of each of the two frame moving tracks 2522 is different from an extending direction of each of the two module moving tracks 2542. The rotating shaft 256 is movably connected to the two module moving tracks 2542. The image capturing module 300 is pivotally connected to the rotating shaft 256 and rotated around the rotating shaft 256 so as to change a direction of the light beam generated by the image capturing module 300. In detail, the two frame moving tracks 2522 are parallel to each other and spaced apart by a first track distance. A top portion of the supporting frame 254 is movably connected to the two frame moving tracks 2522 and configured to position the supporting frame 254 at any location of the two frame moving tracks 2522 by a positioning structure. An extending direction of each of the two frame moving tracks 2522 is parallel to an X-Y plane. The two module moving tracks 2542 are parallel to each other and spaced apart by a second track distance. The second track distance is greater than the first track distance. An extending direction of each of the two module moving tracks 2542 is perpendicular to the X-Y plane. The rotating shaft 256 is disposed on each of the two module moving tracks 2542. In other words, two sides of the image capturing module 300 are connected to two rotating shafts 256, respectively. The two rotating shafts 256 are movably connected to the two module moving tracks 2542 and configured to position the image capturing module 300 at any location of the two module moving tracks 2542 by the positioning structure. The positioning structure may be screws, racks, gears, electrical motors or other positioning mechanisms, and the positioning structure is not limited to the above embodiment. In addition, the rotating electrical device 230 is disposed between the displacement member 220 and the light source seat 250. The rotating electrical device 230 is located at the central axis 240, and the light source seat 250 is rotated by the rotating electrical device 230. The image capturing module 300 connected to the light source seat 250 is synchronously moved with the light source seat 250. In other words, the displacement member 220 is connected to the light source seat 250 by the rotating electrical device 230, so that the light source seat 250 and the image capturing module 300 are synchronously rotated between the second interlocking portion 224b and the third interlocking portion 224c by the rotating electrical device 230. The light source seat 250 is moved along the scanning path and rotated around the central axis 240. Therefore, the scanning path can cover any location in a three-dimensional space formed by the pivotable swinging arm 252, the supporting frame 254 and the rotating electrical device 230 because of the specific structure of the track 212, the swinging track 222, the frame moving tracks 2522, the module moving tracks 2542 and the rotating shafts 256.

The image capturing module 300 is disposed on the light source seat 250 and reciprocated along the scanning path. The image capturing module 300 is configured to generate the light beam emitted from an outside to the patient's mouth. In detail, the image capturing module 300 includes an X-ray tube 310 which generates the light beam. The light beam is an X-ray beam, and the photosensitive member 400 is an X-ray photosensitive film. The scanning path of the X-ray beam can cover any location in the three-dimensional space formed by the pivotable swinging arm 252, the supporting frame 254 and the rotating electrical device 230, so that the X-ray beam of the image capturing module 300 can be emitted toward any direction to capture plural desired images. Accordingly, the present disclosure utilizes the X-ray photosensitive film disposed in the patient's mouth and the freely movable X-ray tube 310 to achieve the quality of the three-dimensional image of cone-beam computed tomography (CBCT), so that the three-dimensional serial focused intraoral digital tomosynthesis scanner 100 can obtain the three-dimensional image via the capturing procedure employing periapical films. The capturing procedure of the three-dimensional serial focused intraoral digital tomosynthesis scanner 100 has a cost similar to the cost of the capturing procedure employing periapical films and less than the cost of a conventional CBCT scan, and it is very suitable for dentist to use.

The photosensitive member 400 is connected to the frame body 200 and positioned in the patient's mouth. The light beam is emitted to the photosensitive member 400. The light beam of the image capturing module 300 is moved along the scanning path corresponding to the photosensitive member 400 so as to generate a plurality of two-dimensional optical images by the image capturing module 300. The photosensitive member 400 has a flaky shape, and the photosensitive member 400 has a flat shape or an arc shape. When the photosensitive member 400 is bitten by the patient, the teeth 102 of the patient are located between the photosensitive member 400 and the image capturing module 300. There is a first distance D1 between the photosensitive member 400 and the image capturing module 300. There is a second distance D2 between the central axis 240 and the image capturing module 300. The first distance D1 is greater than the second distance D2. The photosensitive member 400 is disposed on the third interlocking portion 224c of the displacement member 220 via the fixing seat 226. In addition, the photosensitive member 400 has a flaky shape for closely connect to the teeth 102 of the patient, and the first distance D1 is greater than the second distance D2, so that the rotating angle of the light source seat 250 can capture two-dimensional images of all patient's teeth 102 at a small range of the rotating angle. It is obvious that the rotating angle of the light source seat 250 is relative to the first distance D1, the second distance D2 and the shape of the patient's teeth 102. In one embodiment, the rotating angle is between 60 degrees and 80 degrees.

The image processing module 500 is electrically connected to the image capturing module 300. The image processing module 500 receives the two-dimensional optical images and calculates the two-dimensional optical images to generate a three-dimensional image. The image processing module 500 may be a computer, a mobile device, an electronic instrument or other high-speed processors.

Figure 5:
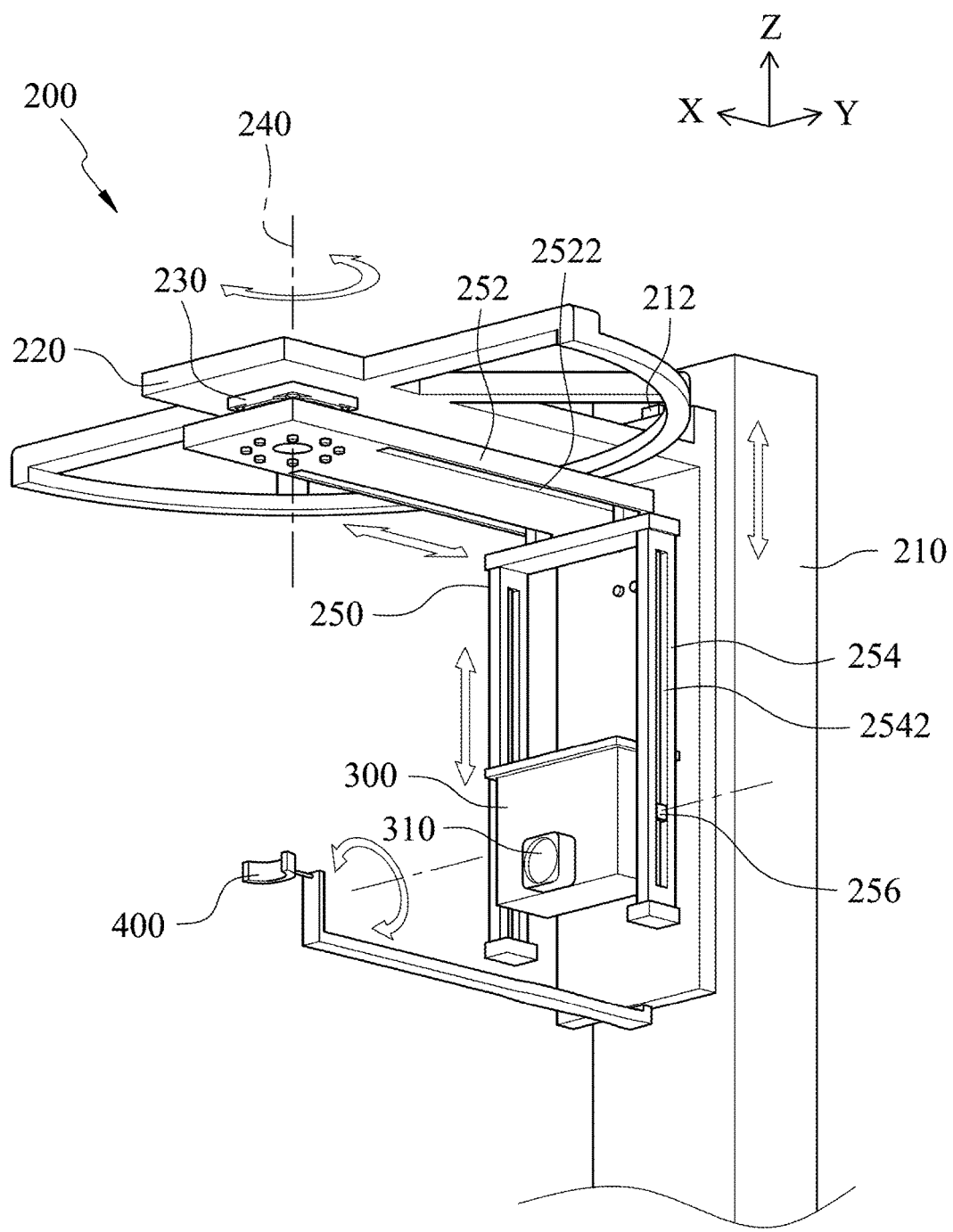
FIG. 5 shows a schematic view of plural moving states of the three-dimensional serial focused intraoral digital tomosynthesis scanner of FIG. 1.

FIG. 5 shows a schematic view of plural moving states of the three-dimensional serial focused intraoral digital tomosynthesis scanner 100 of FIG. 1. The three-dimensional serial focused intraoral digital tomosynthesis scanner 100 has five moving mechanisms which are a first moving mechanism, a second moving mechanism, a third moving mechanism, a fourth moving mechanism and a fifth moving mechanism, respectively. The first moving mechanism represents that the displacement member 220 is moved along the track 212 of the frame seat 210, and the moving direction of the displacement member 220 is parallel to the Z-axis direction (i.e., a vertical movement). The second moving mechanism represents that the light source seat 250 is swung along the swinging track 222 of the displacement member 220 (i.e., a horizontal rotation). The third moving mechanism represents that the supporting frame 254 is moved along the two frame moving tracks 2522 (i.e., a horizontal movement). When the third moving mechanism is performed, the first distance D1 and the second distance D2 are synchronously changed due to the movement of the supporting frame 254. The fourth moving mechanism represents that the image capturing module 300 is moved along the two module moving tracks 2542 (i.e., the vertical movement). The fifth moving mechanism represents that the image capturing module 300 is rotated around the two rotating shafts 256 (i.e., a vertical rotation). The above five moving mechanisms can be operated either manually or automatically. In an automatic mode, the movement or rotation can be performed using electric control, such as an electric motor. Furthermore, the first moving mechanism enables the image capturing module 300 and the photosensitive member 400 to move vertically together so as to dispose the photosensitive member 400 into the mouth of the patient having different heights and postures. The second moving mechanism, the third moving mechanism, the fourth moving mechanism and the fifth moving mechanism enable the image capturing module 300 to move to any desired scanning position for capturing the two-dimensional optical image.

Figure 6:
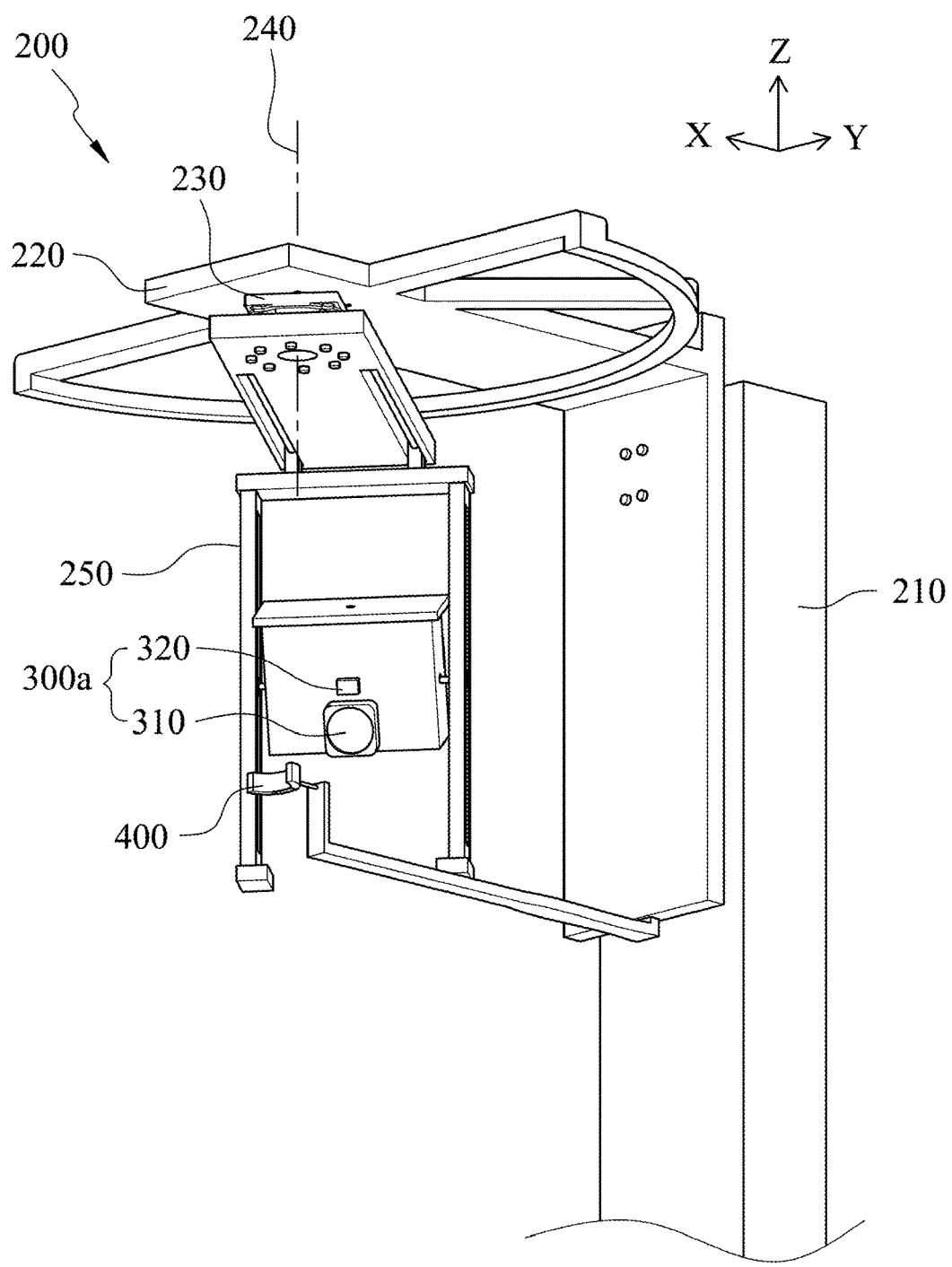
FIG. 6 shows a schematic view of a three-dimensional serial focused intraoral digital tomosynthesis scanner according to another embodiment of the present disclosure.

FIG. 6 shows a schematic view of a three-dimensional serial focused intraoral digital tomosynthesis scanner 100 according to another embodiment of the present disclosure. The three-dimensional serial focused intraoral digital tomosynthesis scanner 100 includes an image capturing module 300a. The image capturing module 300a includes an X-ray tube 310 and a light emitting unit 320. The light emitting unit 320 is adjacent to the X-ray tube 310 and configured to generate a laser beam. The laser beam is emitted to the photosensitive member 400. An irradiating direction of the laser beam of the light emitting unit 320 is parallel to an irradiating direction of the light beam of the X-ray tube 310. The light emitting unit 320 and the X-ray tube 310 are both moved by the light source seat 250. Consequently, the light emitting unit 320 of the present disclosure can allow an operator to know the precise position of the light beam of the X-ray tube 310 irradiated to the outside of the patient's mouth for diagnosis and analysis.

Figure 7:
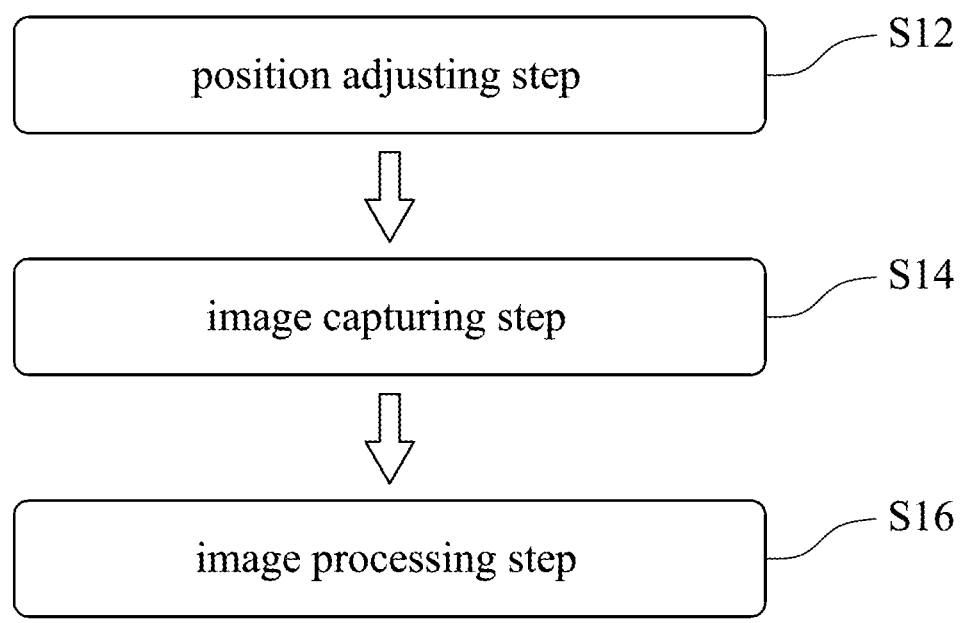
FIG. 7 shows a flow chart of a controlling method of a three-dimensional serial focused intraoral digital tomosynthesis scanner according to one embodiment of the present disclosure.

FIG. 7 shows a flow chart of a controlling method 600 of a three-dimensional serial focused intraoral digital tomosynthesis scanner 100 according to one embodiment of the present disclosure. In FIGS. 1 and 7, the controlling method 600 of the three-dimensional serial focused intraoral digital tomosynthesis scanner 100 provides a position adjusting step S12, an image capturing step S14 and an image processing step S16. The position adjusting step S12 is for moving the image capturing module 300 to a scanning position by the frame body 200 so as to allow the image capturing module 300 to correspond to the photosensitive member 400. The scanning position is corresponding to the patient's mouth and one of the patient's teeth 102. The image capturing step S14 is for generating the light beam emitted from the outside to the patient's mouth and moving the light beam along the scanning path corresponding to the photosensitive member 400 so as to generate the two-dimensional optical images by the image capturing module 300. The image processing step S16 is for calculating the two-dimensional optical images to generate the three-dimensional image by the image processing module 500. Hence, the controlling method 600 of the present disclosure can be achieved by a very simple operation and with high working efficiency. In addition, the controlling method 600 of the present disclosure can not only achieve the dental diagnosis with high resolution and lower radiation dose, but also have a simpler structure, lower cost and a smaller operating space than the conventional CBCT scan. The controlling method 600 of the three-dimensional serial focused intraoral digital tomosynthesis scanner 100 can obtain the high-resolution three-dimensional image which is better than the two-dimensional images only captured by conventional periapical films, thus greatly improving health care quality by using the controlling method 600 applied to the dental diagnosis.

Figure 8:
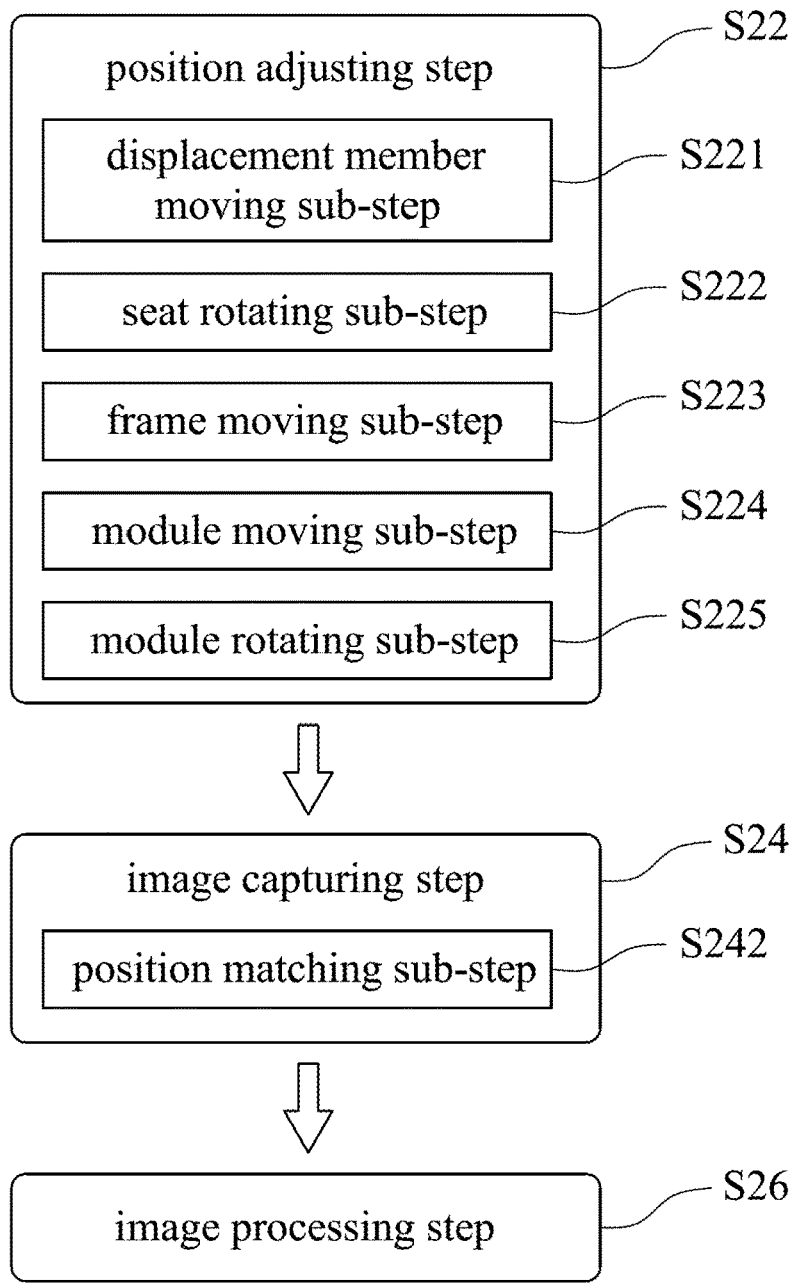
FIG. 8 shows a flow chart of a controlling method of a three-dimensional serial focused intraoral digital tomosynthesis scanner according to another embodiment of the present disclosure.

FIG. 8 shows a flow chart of a controlling method 600a of a three-dimensional serial focused intraoral digital tomosynthesis scanner 100 according to another embodiment of the present disclosure. In FIGS. 1, 6 and 8, the controlling method 600a of the three-dimensional serial focused intraoral digital tomosynthesis scanner 100 provides a position adjusting step S22, an image capturing step S24 and an image processing step S26. The position adjusting step S22 includes a displacement member moving sub-step S221, a seat rotating sub-step S222, a frame moving sub-step S223, a module moving sub-step S224 and a module rotating sub-step S225. The image capturing step S24 includes a position matching sub-step S242. The displacement member moving sub-step S221 is for moving the displacement member 220 along the track 212. When the displacement member 220 is moved to the scanning position, the displacement member 220 is positioned on the track 212 by the positioning member 2242. The seat rotating sub-step S222 is for rotating the light source seat 250 by the rotating electrical device 230 of the frame body 200 and reciprocating the pivotable swinging arm 252 of the light source seat 250 and the image capturing module 300 along the scanning path so as to move the light beam along the scanning path. The frame moving sub-step S223 is for moving the supporting frame 254 of the light source seat 250 along two frame moving tracks 2522 of the pivotable swinging arm 252 of the light source seat 250. When the supporting frame 254 is moved to the scanning position, the supporting frame 254 is positioned on the two frame moving tracks 2522. In addition, the module moving sub-step S224 is for moving the image capturing module 300 along the two module moving tracks 2542 of the supporting frame 254, and when the image capturing module 300 is moved to the scanning position, the image capturing module 300 is positioned on the two module moving tracks 2542. The module rotating sub-step S225 is for rotating the image capturing module 300 around the two rotating shafts 256. When the image capturing module 300 is moved to the scanning position, the image capturing module 300 is positioned on the two rotating shafts 256. Moreover, the position matching sub-step S242 of the image capturing step S24 is for emitting a laser beam to the photosensitive member 400 via the light emitting unit 320 so as to allow the light beam of the image capturing module 300 and the laser beam to correspond to the patient's mouth, and then moving the light beam along the scanning path corresponding to the photosensitive member 400 so as to generate the two-dimensional optical images by the image capturing module 300. The image processing step S26 is for calculating the two-dimensional optical images to generate the three-dimensional image by the image processing module 500. Therefore, the controlling method 600a of the three-dimensional serial focused intraoral digital tomosynthesis scanner 100 of the present disclosure can output the high-resolution three-dimensional image and reduce complexity of operating steps of the conventional CBCT scan, thereby increasing high working efficiency. The controlling method 600a of the three-dimensional serial focused intraoral digital tomosynthesis scanner 100 has a cost and an operating space which is similar to the cost and the operating space of the capturing procedure employing conventional periapical films. The controlling method 600a of the present disclosure can not only achieve the dental diagnosis with high resolution and lower radiation dose, but also have a simpler structure, lower cost and a smaller operating space than the conventional CBCT scan. The controlling method 600a of the three-dimensional serial focused intraoral digital tomosynthesis scanner 100 can obtain the high-resolution three-dimensional image which is better than the two-dimensional images only captured by conventional periapical films, thus greatly improving health care quality by using the controlling method 600a applied to the dental diagnosis.

Figure 9:
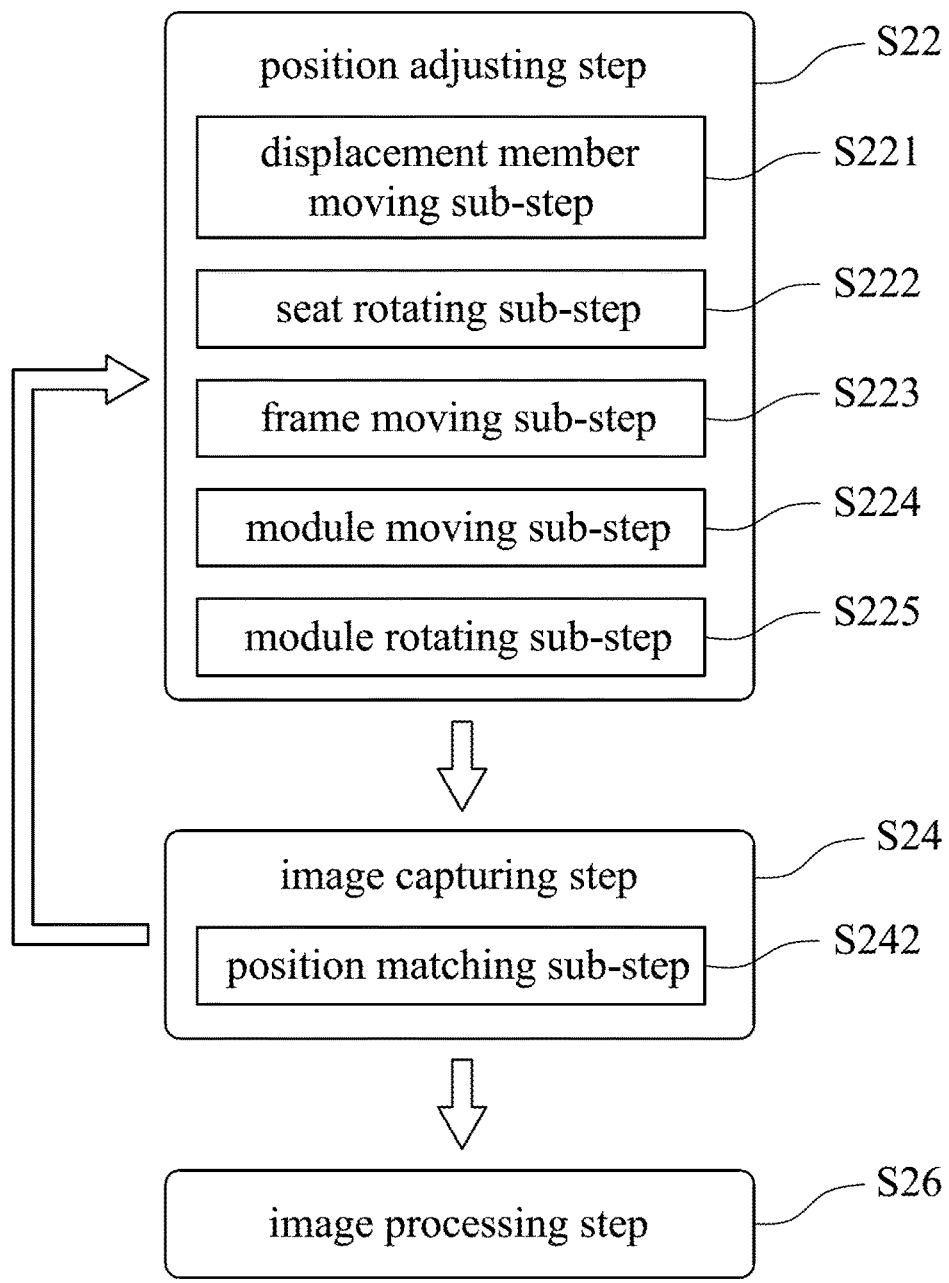
FIG. 9 shows a flow chart of a controlling method of a three-dimensional serial focused intraoral digital tomosynthesis scanner according to further another embodiment of the present disclosure.
Figure 10:
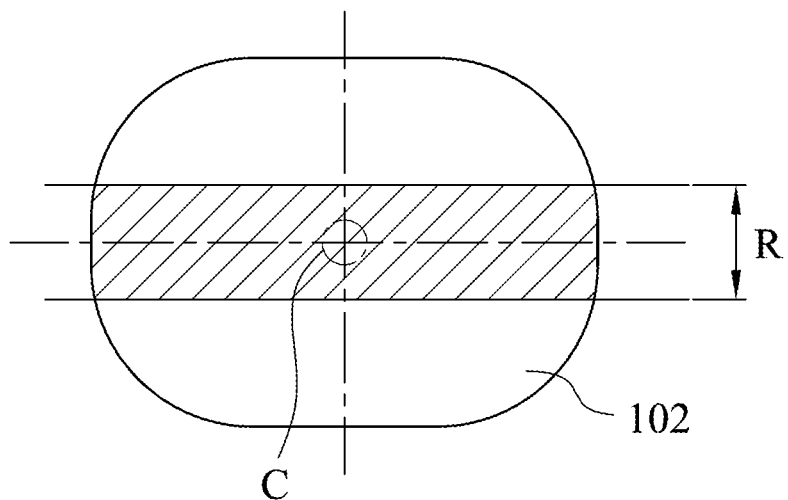
FIG. 10 shows a schematic view of a scanning region of a tooth generated by the controlling method of the three-dimensional serial focused intraoral digital tomosynthesis scanner of FIG. 9 when the tooth is scanned one time and a rotating angle is ±60 degrees.
Figure 11:
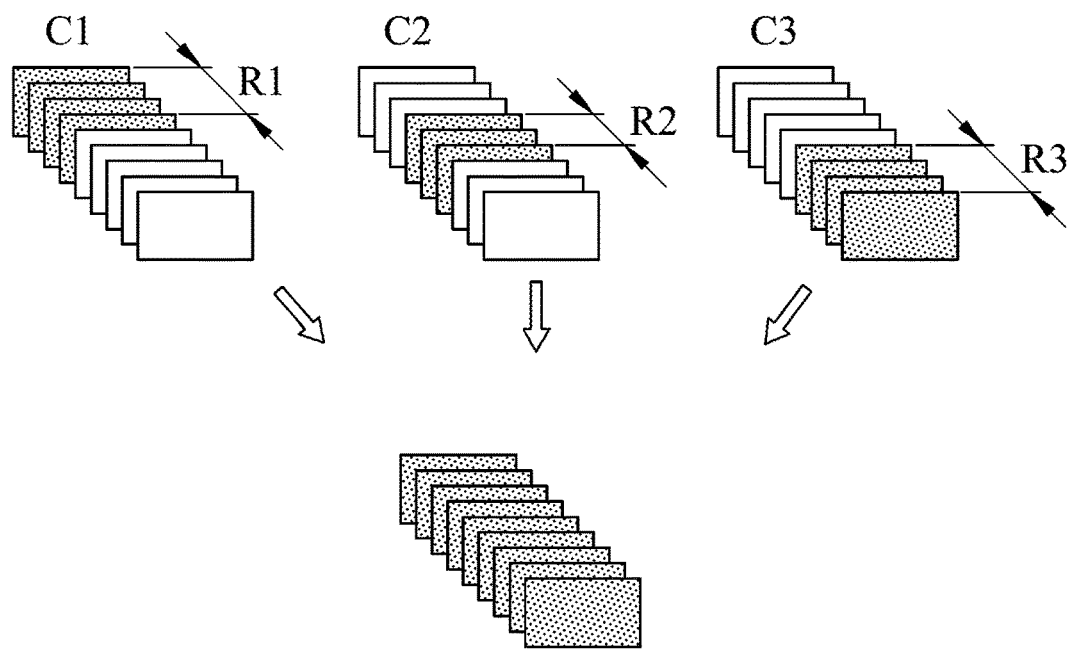
FIG. 11 shows a schematic view of a combining image procedure conducted by the controlling method of the three-dimensional serial focused intraoral digital tomosynthesis scanner of FIG. 9.
Figure 12:
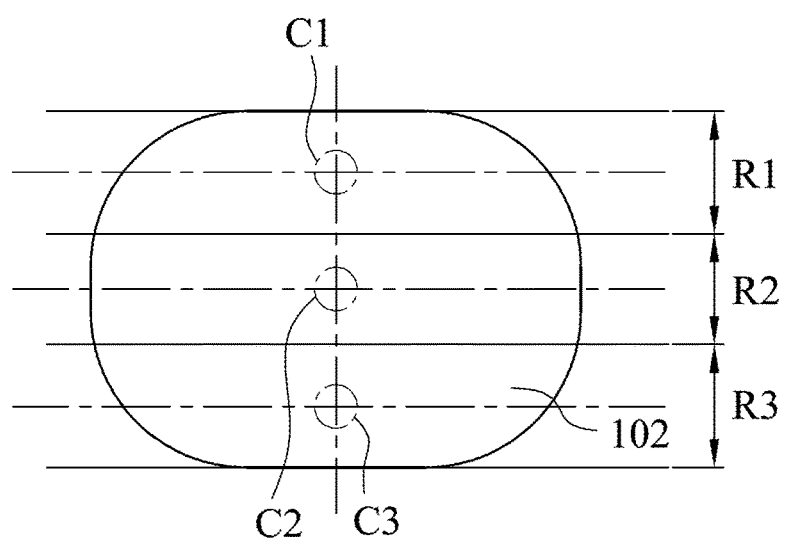
FIG. 12 shows a schematic view of a combined image of the tooth by using the controlling method of the three-dimensional serial focused intraoral digital tomosynthesis scanner of FIG. 11 when the tooth is scanned three times and a rotating angle is ±60 degrees.

FIG. 9 shows a flow chart of a controlling method 600b of a three-dimensional serial focused intraoral digital tomosynthesis scanner 100 according to further another embodiment of the present disclosure; FIG. 10 shows a schematic view of a scanning region R of a tooth 102 generated by the controlling method 600b of the three-dimensional serial focused intraoral digital tomosynthesis scanner 100 of FIG. 9 when the tooth 102 is scanned one time and a rotating angle is ±60 degrees; FIG. 11 shows a schematic view of a combining image procedure conducted by the controlling method 600b of the three-dimensional serial focused intraoral digital tomosynthesis scanner 100 of FIG. 9; and FIG. 12 shows a schematic view of a combined image of the tooth 102 by using the controlling method 600b of the three-dimensional serial focused intraoral digital tomosynthesis scanner 100 of FIG. 11 when the tooth 102 is scanned three times and a rotating angle is ±60 degrees. In FIGS. 2, 5 and 9-12, the controlling method 600b of the three-dimensional serial focused intraoral digital tomosynthesis scanner 100 provides a position adjusting step S22, an image capturing step S24 and an image processing step S26. The details of the position adjusting step S22, the image capturing step S24 and the image processing step S26 are the same as the embodiments of FIG. 8. The difference between FIG. 9 and FIG. 8 embodiments is that, in FIG. 9, the image capturing step S24 is feedback connected to the position adjusting step S22. In other words, the position adjusting step S22 and the image capturing step S24 of the controlling method 600b are repeatedly conducted until the tooth 102 of the patient is scanned clearly.

Figure 13:
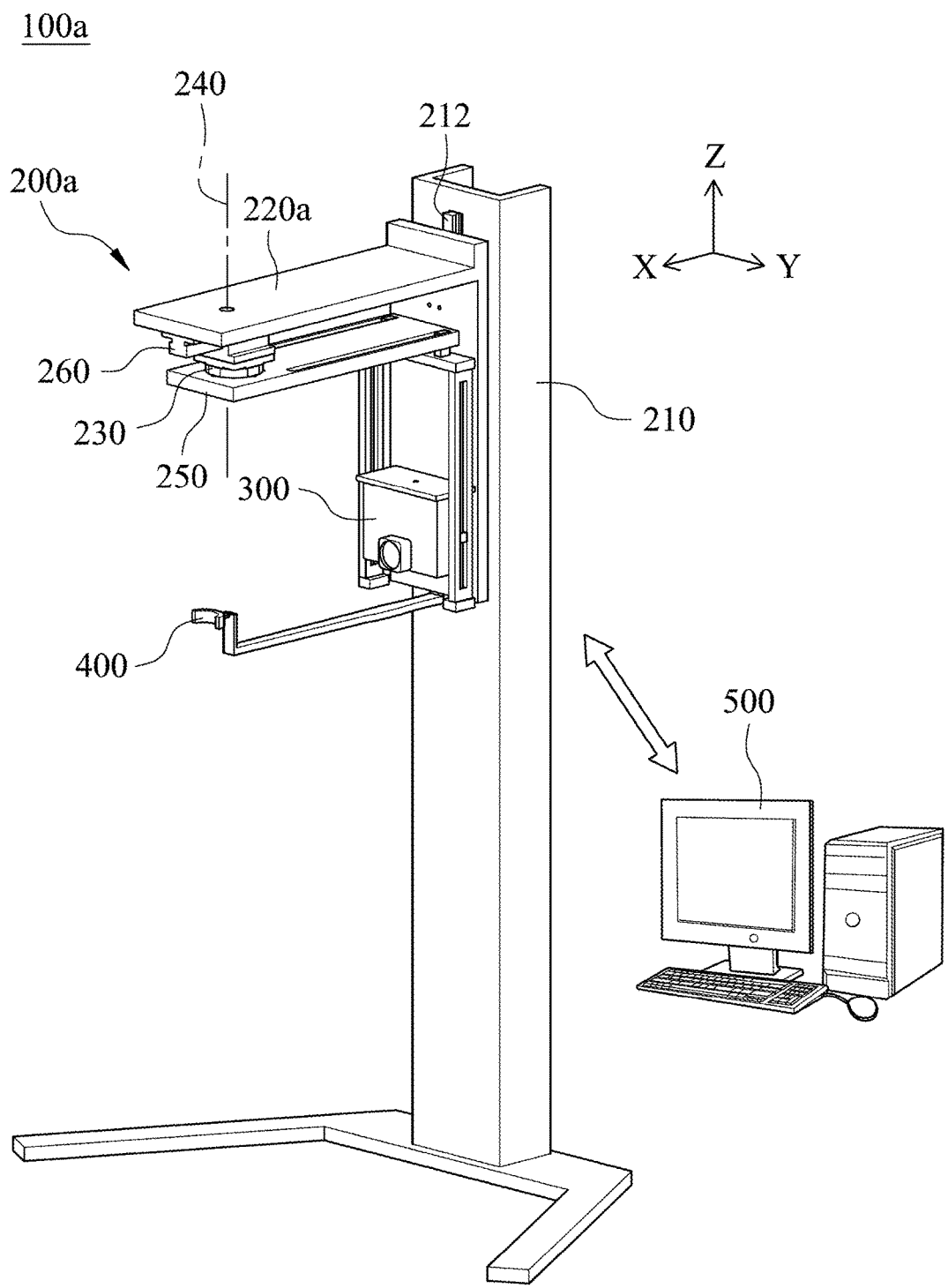
FIG. 13 shows a schematic view of a three-dimensional serial focused intraoral digital tomosynthesis scanner according to further another embodiment of the present disclosure.
Figure 14:
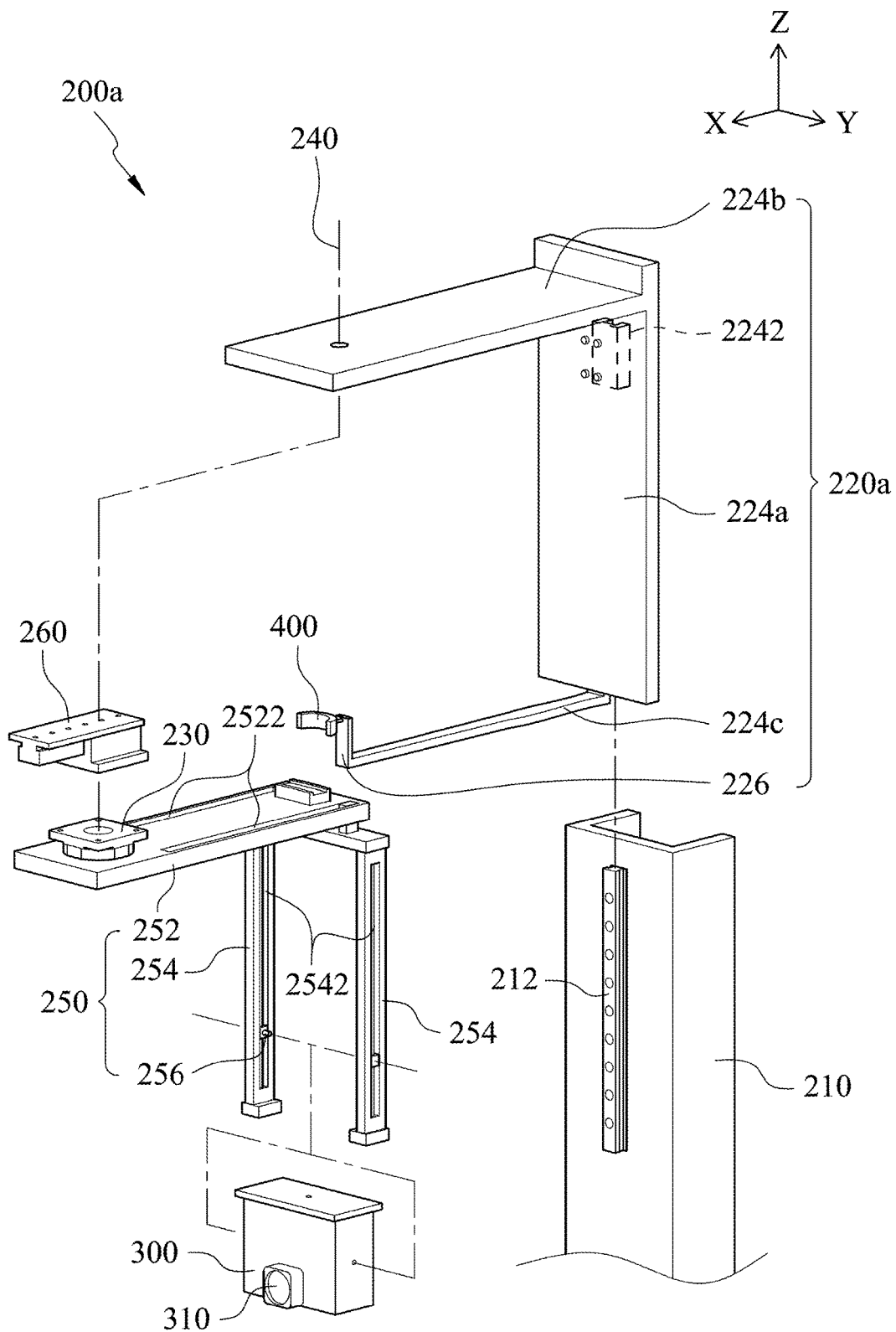
FIG. 14 shows an exploded view of the three-dimensional serial focused intraoral digital tomosynthesis scanner of FIG. 13.

For example, when the tooth 102 is scanned one time and a rotating angle is ±60 degrees by the controlling method 600b, the clear scanning region R parallel to an X-axis direction is about 3 mm, as shown in FIG. 10. The clear scanning region R is about ±1.5 mm relative to a virtual center C which is overlapped with the central axis 240. The central axis 240 and the virtual center C are both corresponding to the tooth 102. In general, an average thickness of an adult tooth is about 8 to 10 mm, and a conventional computed tomography scan cannot satisfy the clinical requirement. However, the controlling method 600b of the three-dimensional serial focused intraoral digital tomosynthesis scanner 100 of the present disclosure can utilize a combining image procedure to combine a series of two-dimensional images to form a clear three-dimensional image when the tooth 102 is scanned three times and the rotating angle is ±60 degrees, as shown in FIGS. 13 and 14. The position adjusting step S22 and the image capturing step S24 of the controlling method 600b are performed three times, and then a first virtual center C1, a second virtual center C2, a third virtual center C3 are obtained sequentially. Three scanning paths which are respectively corresponding to the first virtual center C1, the second virtual center C2 and the third virtual center C3 are generated at the same time. When the position adjusting step S22 and the image capturing step S24 of the controlling method 600b are performed for the first time, the image processing module 500 simulates the central axis 240 to correspond to the first virtual center C1 and generates a first scanning path. Then, the image capturing module 300 scans the tooth 102 along the first scanning path to generate a plurality of two-dimensional optical images in a first scanning region R1. When the position adjusting step S22 and the image capturing step S24 of the controlling method 600b are performed for the second time, the image processing module 500 simulates the central axis 240 to correspond to the second virtual center C2 and generates a second scanning path. Then, the image capturing module 300 scans the tooth 102 along the second scanning path to generate a plurality of two-dimensional optical images in a second scanning region R2. When the position adjusting step S22 and the image capturing step S24 of the controlling method 600b are performed for the third time, the image processing module 500 simulates the central axis 240 to correspond to the third virtual center C3 and generates a third scanning path. Then, the image capturing module 300 scans the tooth 102 along the third scanning path to generate a plurality of two-dimensional optical images in a third scanning region R3. In one embodiment, the thickness of the tooth 102 is 6 mm, and an angular interval of the rotating angle is one degree. The rotating angle is ±60 degrees (i.e., the rotating angle is 120 degrees). When the position adjusting step S22 and the image capturing step S24 of the controlling method 600b are performed for each time, the two-dimensional optical images are generated, and a number of the two-dimensional optical images is 700. The number of the two-dimensional optical images corresponding to the tooth 102 is 201. Due to the different positions of the first virtual center C1, the second virtual center C2 and the third virtual center C3, the clear regions of the tooth 102 are also different. In the first scanning path, the clear region of the tooth 102 is the first scanning region R1 corresponding to the first virtual center C1. The number of the two-dimensional optical images in the first scanning region R1 is 67. In the second scanning path, the clear region of the tooth 102 is the second scanning region R2 corresponding to the second virtual center C2. The number of the two-dimensional optical images in the second scanning region R2 is 67. In the third scanning path, the clear region of the tooth 102 is the third scanning region R3 corresponding to the third virtual center C3. The number of the two-dimensional optical images in the third scanning region R3 is 67. The image processing module 500 sequentially combines the images in these three scanning regions R1, R2, R3 to form a new group of the two-dimensional optical images. The number of the new group of the two-dimensional optical images is 201, and all two-dimensional optical images are clear and distinct. Furthermore, because of the movement of the central axis 240, a source-to-object distance (SOD) between the tooth 102 and the image capturing module 300 is changed during the combining image procedure, so that the images in the three scanning regions R1, R2, R3 should be calibrated to make sure that the magnification rates of the images in the three scanning regions R1, R2, R3 are equal to each other. After calibrating, the images in the three scanning regions R1 R2, R3 can be perfectly arranged together to form the three-dimensional image. In addition, the number of scanning times is related to the rotating angle. The smaller the rotating angle is, the larger number of scanning times is. The operator can freely determine the rotating angle and the number of scanning times according to the condition of the tooth 102 of the patient. Consequently, the position adjusting step S22 and the image capturing step S24 of the controlling method 600b of the present disclosure are repeatedly conducted under conditions of specific scanning times and the specific rotating angle until the tooth 102 of the patient is scanned clearly. If the two-dimensional optical images and the three-dimensional image are all clear and distinct, the dental diagnosis can be performed more accurately, and a chance of misjudgment may be greatly reduced.

Figure 15:
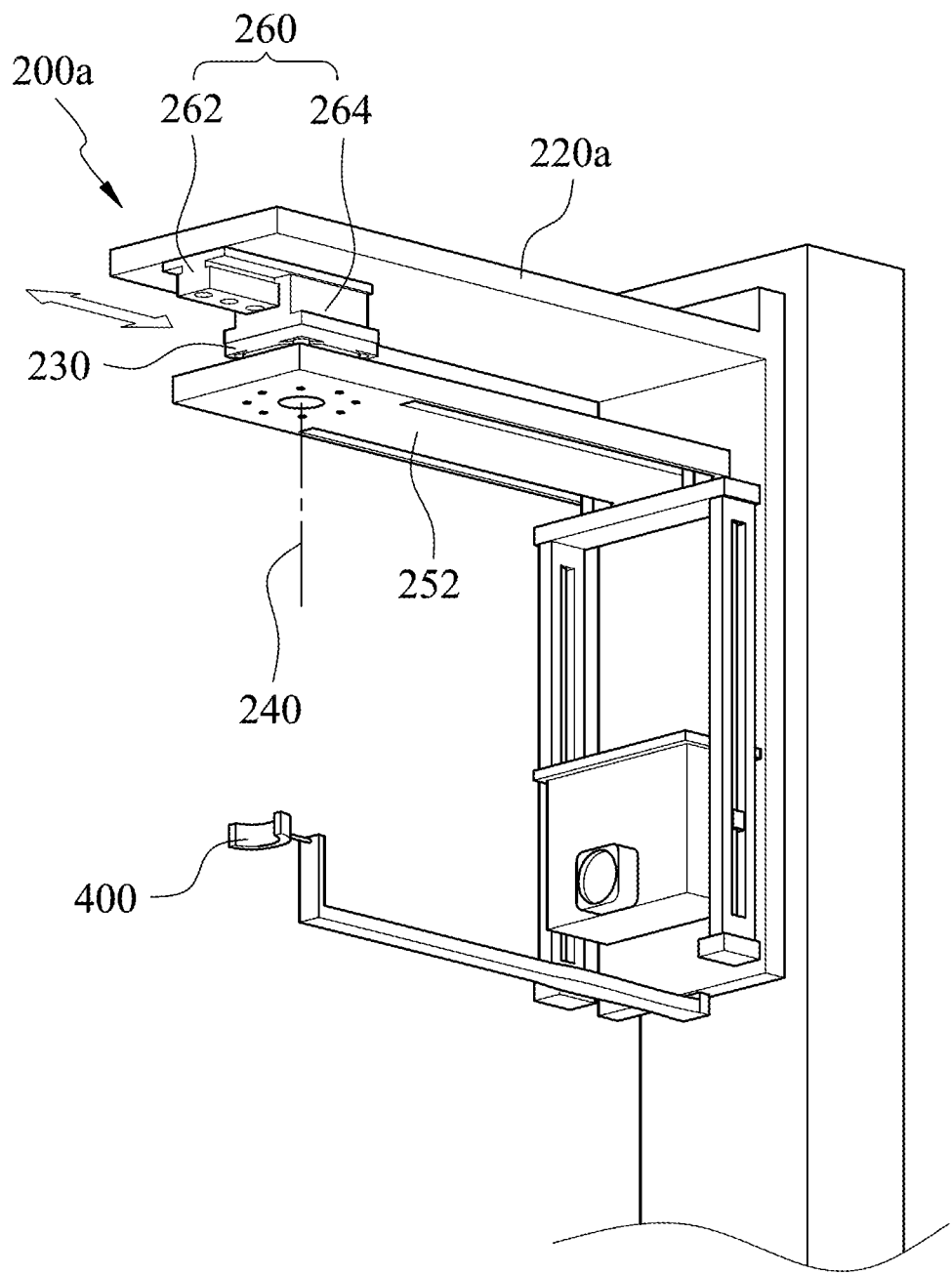
FIG. 15 shows a schematic view of a moving state of the three-dimensional serial focused intraoral digital tomosynthesis scanner of FIG. 13.

FIG. 13 shows a schematic view of a three-dimensional serial focused intraoral digital tomosynthesis scanner 100a according to further another embodiment of the present disclosure; FIG. 14 shows an exploded view of the three-dimensional serial focused intraoral digital tomosynthesis scanner 100a of FIG. 13; and FIG. 15 shows a schematic view of a moving state of the three-dimensional serial focused intraoral digital tomosynthesis scanner 100a of FIG. 13. The three-dimensional serial focused intraoral digital tomosynthesis scanner 100a includes a frame body 200a, an image capturing module 300, a photosensitive member 400 and an image processing module 500.

In FIGS. 13-15, the details of the image capturing module 300, the photosensitive member 400 and the image processing module 500 are the same as the embodiments of FIG. 2, and will not be described again herein. In FIG. 14, the three-dimensional serial focused intraoral digital tomosynthesis scanner 100a further includes the frame body 200a, and the frame body 200a further includes a sliding structure 260 and a displacement member 220a without a swinging track 222. The sliding structure 260 is connected between the displacement member 220a and the light source seat 250. The sliding structure 260 includes a sliding track 262 and a sliding member 264. The sliding track 262 is connected to the displacement member 220a. The sliding member 264 is connected to the light source seat 250 and movably disposed on the sliding track 262. The central axis 240 is corresponding to the light source seat 250 and the sliding member 264. The sliding member 264 and the light source seat 250 are moved together along the sliding track 262 so as to synchronously move the central axis 240, as shown in FIG. 15. Moreover, the frame body 200a includes a rotating electrical device 230 disposed between the sliding member 264 and the light source seat 250. The rotating electrical device 230 is located at the central axis 240. The light source seat 250 is rotated by the rotating electrical device 230, and the rotating electrical device 230 is moved along the sliding track 262 by the sliding member 264. Accordingly, the three-dimensional serial focused intraoral digital tomosynthesis scanner 100a of the present disclosure can change the position of the central axis 240 during the combining image procedure. When the central axis 240 is moved, the virtual center C is synchronously moved together with the central axis 240. The rotating electrical device 230 is positioned on the movable sliding member 264 of the sliding structure 260 to achieve a multifocal effect, as shown in FIGS. 11 and 12. The image capturing module 300 scans the tooth 102 three times according to three different scanning paths to generate three groups of plural two-dimensional optical images in the three scanning regions R1 R2, R3, respectively. The three scanning paths are corresponding to the three virtual centers C1, C2, C3, respectively. The number of the two-dimensional optical images in each of the three scanning regions R1, R2, R3 is 67. The image processing module 500 sequentially combines the images in these three scanning regions R1, R2, R3 to form a new group of the two-dimensional optical images which are all clear and distinct. Finally, the images in the three scanning regions R1, R2, R3 can be perfectly arranged together to form the three-dimensional image.

Figure 16:
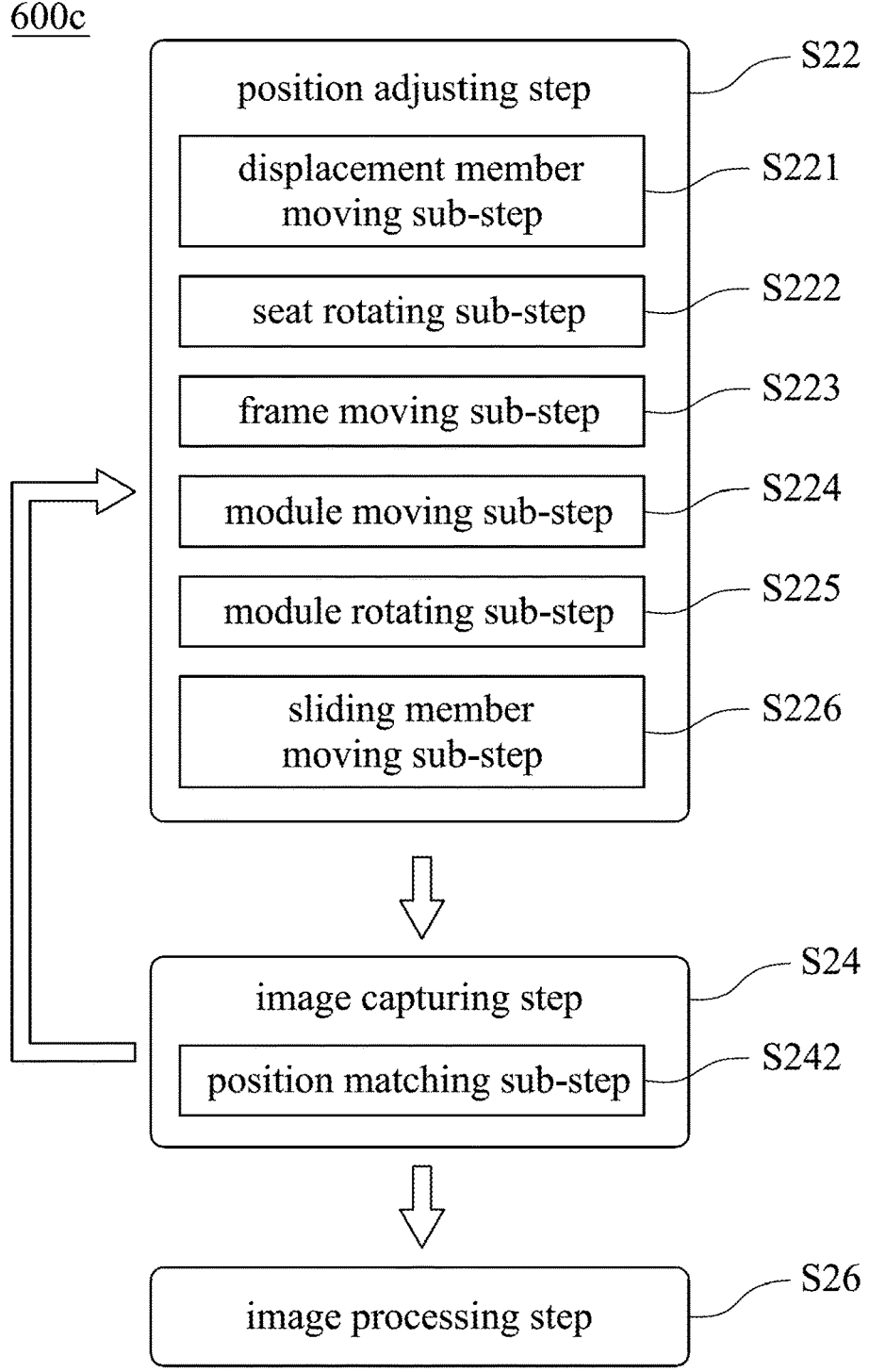
FIG. 16 shows a flow chart of a controlling method of a three-dimensional serial focused intraoral digital tomosynthesis scanner according to still further another embodiment of the present disclosure.

FIG. 16 shows a flow chart of a controlling method 600c of a three-dimensional serial focused intraoral digital tomosynthesis scanner 100a according to still further another embodiment of the present disclosure. The controlling method 600c provides a position adjusting step S22, an image capturing step S24 and an image processing step S26. The details of the image capturing step S24 and an image processing step S26 are the same as the embodiments of FIG. 9, and will not be described again herein. In FIGS. 15 and 16, the position adjusting step S22 further includes a sliding member moving sub-step S226. The sliding member moving sub-step S226 is for moving a sliding member 264 of a sliding structure 260 of the frame body 200a along a sliding track 262 of the sliding structure 260 so as to synchronously move the light source seat 250, the sliding member 264 and the central axis 240. The image capturing module 300 is reciprocated by the light source seat 250 so as to generate a plurality of scanning paths. The controlling method 600c of the present disclosure is configured to scan the tooth 102 three times according to three different scanning paths to generate three groups of plural two-dimensional optical images, respectively. The number of execution times of the sliding member moving sub-step S226 is equal to the number of scanning paths. The number of execution times of the seat rotating sub-step S222 is equal to the number of execution times of the sliding member moving sub-step S226. Accordingly, the controlling method 600c of the present disclosure can achieve the multifocal effect and generate the two-dimensional optical images and the three-dimensional image which are all clear and distinct, so that the dental diagnosis can be performed more accurately, and the chance of misjudgment may be greatly reduced.

According to the aforementioned embodiments and examples, the advantages of the present disclosure are described as follows.

1. The three-dimensional serial focused intraoral digital tomosynthesis scanner and the controlling method thereof of the present disclosure can be implemented by a very simple operation and with high working efficiency.

2. The three-dimensional serial focused intraoral digital tomosynthesis scanner and the controlling method thereof of the present disclosure can output the high-resolution three-dimensional image and reduce complexity of operating steps of the conventional CBCT scan, thereby increasing high working efficiency. In addition, the present disclosure can not only achieve the dental diagnosis with high resolution and lower radiation dose, but also have a simpler structure, lower cost and a smaller operating space than the conventional CBCT scan.

3. The three-dimensional serial focused intraoral digital tomosynthesis scanner and the controlling method thereof of the present disclosure has a cost and an operating space which is similar to the cost and the operating space of the capturing procedure employing conventional periapical films. The present disclosure can obtain the high-resolution three-dimensional image which is better than the two-dimensional images only captured by conventional periapical films, thus greatly improving health care quality by using the controlling method applied to the dental diagnosis.

4. The three-dimensional serial focused intraoral digital tomosynthesis scanner and the controlling method thereof of the present disclosure can achieve the multifocal effect and generate the two-dimensional optical images and the three-dimensional image which are all clear and distinct, so that the dental diagnosis can be performed more accurately, and the chance of misjudgment may be greatly reduced.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A three-dimensional serial focused intraoral digital tomosynthesis scanner for scanning a patient's mouth, the three-dimensional serial focused intraoral digital tomosynthesis scanner comprising:
   a frame body comprising a central axis and a light source seat, wherein the light source seat is moved along a scanning path and rotated around the central axis;
   an image capturing module disposed on the light source seat and reciprocated along the scanning path, wherein the image capturing module is configured to generate a light beam emitted from an outside to the patient's mouth;
   a photosensitive member connected to the frame body and positioned in the patient's mouth, wherein the light beam is emitted to the photosensitive member, the light beam is moved along the scanning path corresponding to the photosensitive member so as to generate a plurality of two-dimensional optical images by the image capturing module, and the photosensitive member has a flaky shape; and
   an image processing module electrically connected to the image capturing module, wherein the image processing module receives the two-dimensional optical images and calculates the two-dimensional optical images to generate a three-dimensional image.

2. The three-dimensional serial focused intraoral digital tomosynthesis scanner of claim 1, wherein there is a first distance between the photosensitive member and the image capturing module, there is a second distance between the central axis and the image capturing module, and the first distance is greater than the second distance.

3. The three-dimensional serial focused intraoral digital tomosynthesis scanner of claim 1, wherein the frame body further comprises:
   a frame seat comprising a track extending in a Z-axis direction; and
   a displacement member movably connected to the frame seat and positioned on the track by a positioning member;
   wherein the photosensitive member is disposed on the displacement member.

4. The three-dimensional serial focused intraoral digital tomosynthesis scanner of claim 3, wherein the frame body further comprises:
   a rotating electrical device disposed between the displacement member and the light source seat, wherein the rotating electrical device is located at the central axis, and the light source seat is rotated by the rotating electrical device.

5. The three-dimensional serial focused intraoral digital tomosynthesis scanner of claim 4, wherein the light source seat comprises:
   a pivotable swinging arm connected to the rotating electrical device; and
   a supporting frame connected to the pivotable swinging arm, wherein the image capturing module is movably disposed on the supporting frame, the pivotable swinging arm is rotated by the rotating electrical device to allow the image capturing module to reciprocate along the scanning path so as to move the light beam along the scanning path.

6. The three-dimensional serial focused intraoral digital tomosynthesis scanner of claim 5, wherein the displacement member comprises a swinging track connected to the pivotable swinging arm, the pivotable swinging arm is rotated around the central axis at a rotating angle and configured to swing along the swinging track, and the rotating angle is smaller than or equal to 180 degrees.

7. The three-dimensional serial focused intraoral digital tomosynthesis scanner of claim 5, wherein the displacement member comprises:
   a first interlocking portion connected to the track, wherein an extending direction of the first interlocking portion is parallel to the Z-axis direction;
   a second interlocking portion connected to one end of the first interlocking portion, wherein an extending direction of the second interlocking portion is perpendicular to the Z-axis direction, and the rotating electrical device is disposed on the second interlocking portion;
   a third interlocking portion connected to the other end of the first interlocking portion, wherein an extending direction of the third interlocking portion is parallel to the extending direction of the second interlocking portion, the pivotable swinging arm, the supporting frame and the image capturing module are synchronously rotated between the second interlocking portion and the third interlocking portion by the rotating electrical device; and
   a fixing seat connected between the third interlocking portion and the photosensitive member.

8. The three-dimensional serial focused intraoral digital tomosynthesis scanner of claim 5, wherein,
   the pivotable swinging arm comprises at least one frame moving track, and the supporting frame is restrictedly moved along the frame moving track; and
   the supporting frame comprises at least one module moving track, the image capturing module is restrictedly moved along the module moving track, and an extending direction of the frame moving track is different from an extending direction of the module moving track.

9. The three-dimensional serial focused intraoral digital tomosynthesis scanner of claim 8, wherein the light source seat further comprises:
   a rotating shaft movably connected to the module moving track, wherein the image capturing module is pivotally connected to the rotating shaft and rotated around the rotating shaft so as to change a direction of the light beam.

10. The three-dimensional serial focused intraoral digital tomosynthesis scanner of claim 3, wherein the frame body further comprises:
    a sliding structure connected between the displacement member and the light source seat, and the sliding structure comprising:

a sliding track connected to the displacement member; and a sliding member connected to the light source seat and movably disposed on the sliding track;

wherein the central axis is corresponding to the light source seat and the sliding member, and the sliding member and the light source seat are moved together along the sliding track so as to synchronously move the central axis.

11. The three-dimensional serial focused intraoral digital tomosynthesis scanner of claim 10, wherein the frame body further comprises:

a rotating electrical device disposed between the sliding member and the light source seat, wherein the rotating electrical device is located at the central axis, the light source seat is rotated by the rotating electrical device, and the rotating electrical device is moved along the sliding track by the sliding member.

12. The three-dimensional serial focused intraoral digital tomosynthesis scanner of claim 1, wherein the image capturing module comprises an X-ray tube which generates the light beam, the light beam is an X-ray beam, and the photosensitive member is an X-ray photosensitive film.

13. The three-dimensional serial focused intraoral digital tomosynthesis scanner of claim 12, wherein the image capturing module further comprises:

a light emitting unit adjacent to the X-ray tube, wherein the light emitting unit is configured to generate a laser beam, the laser beam is emitted to the photosensitive member, an irradiating direction of the laser beam is parallel to an irradiating direction of the light beam, and the light emitting unit and the X-ray tube are both moved by the light source seat.

14. A controlling method of the three-dimensional serial focused intraoral digital tomosynthesis scanner of claim 1, the controlling method comprising:

providing a position adjusting step, wherein the position adjusting step is for moving the image capturing module to a scanning position by the frame body so as to allow the image capturing module to correspond to the photosensitive member;

providing an image capturing step, wherein the image capturing step is for generating the light beam emitted from the outside to the patient's mouth and moving the light beam along the scanning path corresponding to the photosensitive member so as to generate the two-dimensional optical images by the image capturing module; and providing an image processing step, wherein the image processing step is for calculating the two-dimensional optical images to generate the three-dimensional image by the image processing module.

15. The controlling method of the three-dimensional serial focused intraoral digital tomosynthesis scanner of claim 14, wherein the position adjusting step comprises:

providing a displacement member moving sub-step, wherein the displacement member moving sub-step is for moving a displacement member along the track, and when the displacement member is moved to the scanning position, the displacement member is positioned on the track by a positioning member; and providing a seat rotating sub-step, wherein the seat rotating sub-step is for rotating the light source seat by a rotating electrical device of the frame body and reciprocating a pivotable swinging arm of the light source seat and the image capturing module along the scanning path so as to move the light beam along the scanning path.

16. The controlling method of the three-dimensional serial focused intraoral digital tomosynthesis scanner of claim 15, wherein the position adjusting step further comprises:

providing a sliding member moving sub-step, wherein the sliding member moving sub-step is for moving a sliding member of a sliding structure of the frame body along a sliding track so as to synchronously move the light source seat, the sliding member and the central axis;

wherein the image capturing module is reciprocated by the light source seat so as to generate a plurality of scanning paths.

17. The controlling method of the three-dimensional serial focused intraoral digital tomosynthesis scanner of claim 16, wherein a number of execution times of the sliding member moving sub-step is equal to a number of scanning paths, and a number of execution times of the seat rotating sub-step is equal to the number of execution times of the sliding member moving sub-step.

18. The controlling method of the three-dimensional serial focused intraoral digital tomosynthesis scanner of claim 14, wherein the position adjusting step comprises:

providing a frame moving sub-step, wherein the frame moving sub-step is for moving a supporting frame along a frame moving track of a pivotable swinging arm, and when the supporting frame is moved to the scanning position, the supporting frame is positioned on the frame moving track; and providing a module moving sub-step, wherein the module moving sub-step is for moving the image capturing module along a module moving track of the supporting frame, and when the image capturing module is moved to the scanning position, the image capturing module is positioned on the module moving track.

19. The controlling method of the three-dimensional serial focused intraoral digital tomosynthesis scanner of claim 14, wherein the position adjusting step comprises:

providing a module rotating sub-step, wherein the module rotating sub-step is for rotating the image capturing module around a rotating shaft, and when the image capturing module is moved to the scanning position, the image capturing module is positioned on the rotating shaft.

20. The controlling method of the three-dimensional serial focused intraoral digital tomosynthesis scanner of claim 14, wherein the image capturing step comprises:

providing a position matching sub-step, wherein the position matching sub-step is for emitting a laser beam to the photosensitive member via a light emitting unit so as to allow the light beam of the image capturing module and the laser beam to correspond to the patient's mouth.

* * * * *